(12) United States Patent
Yan et al.

(10) Patent No.: US 9,178,170 B2
(45) Date of Patent: Nov. 3, 2015

(54) FIBER-BASED ORGANIC ELECTROCHEMICAL TRANSISTOR

(71) Applicant: The Hong Kong Polytechnic University, Kowloon, Hong Kong (CN)

(72) Inventors: Feng Yan, Hong Kong (CN); Caizhi Liao, Hong Kong (CN)

(73) Assignee: THE HONG KONG POLYTECHNIC UNIVERSITY, Hung Hom, Kowloon, Hong Kong (CN)

( * ) Notice: Subject to any disclaimer, the term of this patent is extended or adjusted under 35 U.S.C. 154(b) by 129 days.

(21) Appl. No.: 14/066,783

(22) Filed: Oct. 30, 2013

(65) Prior Publication Data

US 2015/0115227 A1    Apr. 30, 2015

(51) Int. Cl.
*H01L 29/08* (2006.01)
*H01L 21/00* (2006.01)
*H01L 51/05* (2006.01)
*G01N 27/414* (2006.01)

(52) U.S. Cl.
CPC ........ *H01L 51/0558* (2013.01); *G01N 27/4145* (2013.01)

(58) Field of Classification Search
CPC .......................... H01L 51/0558; G01N 27/4145
USPC .............................................. 257/40; 438/49
See application file for complete search history.

(56) References Cited

U.S. PATENT DOCUMENTS

2009/0040587 A1* 2/2009 Kugler ........................ 359/265
2010/0163283 A1* 7/2010 Hamedi et al. ............... 174/254

OTHER PUBLICATIONS

Danilo De Rossi; "Electronic Textiles a logical step", *Nature Materials*, vol. 6, pp. 328-329, (May 2007).
M. Hamedi et al.; "Towards woven logic from organic electronic fibres", *Nature Materials*, vol. 6, pp. 357-362, (May 2007).
C. Müller et al.; "Woven Electrochemical Transistors on Silk Fibers", *Advanced Materials*, vol. 23, pp. 898-901 (2011).
X. Tao et al.; "Geometry Pattern for the Wire Organic Electrochemical Textile Transistor", *J. of the Electrochemical Soc.*, vol. 158 (5), pp. H572-H577, (Mar. 23, 2011).
G. Tarabella et al.; "A single cotton fiber organic electrochemical transistor for liquid electrolyte saline sensing", *J. of Materials Chemistry*, vol. 22, pp. 23830-23834, (2012).
M. Hamedi et al.; "Fiber-Embedded Electrolyte-Gated Field-Effect Transistors for e-Textiles", *Advanced materials*, vol. 21, pp. 573-577, (2009).
A. Bonfiglio et al.; "Organic Field Effect Transistors for Textile Applications", *IEEE Transactions on Information Technology in Biomedicine*, vol. 9, No. 3, pp. 319-324, (Sep. 2005).

(Continued)

*Primary Examiner* — Long K Tran
(74) *Attorney, Agent, or Firm* — Leydig, Voit & Mayer, Ltd.

(57) ABSTRACT

An organic electrochemical transistor (OECT) that may be used as a biosensor is built up by layers applied to a monofilament. A first conducting layer applied to the monofilament includes generally cylindrical source and drain contacts with a gap therebetween. An electro-active layer of an organic material altering its electrical conductivity through a change in redox state is in electrical contact with the source and drain contacts, and has a transistor channel interface for contacting an electrolyte. A gate electrode is spaced apart from the first monofilament, and may comprise a cylindrical layer built up on another length of monofilament.

15 Claims, 9 Drawing Sheets

(56) References Cited

OTHER PUBLICATIONS

J. B. Lee et al.; "Organic Transistors on Fiber: A first step towards electronic textiles", *IEEE Dept. of Electrical Eng. and Computer Sciences*, Univ. of CA, Berkeley, (2003).

M. Maccioni et al.; "Towards the textile transistor: Assembly and characterization of an organic field effect transistor with a cylindrical geometry", *Applied Physics Letters*, vol. 89, pp. 143515-1-143515-3, (2006).

J. B. Lee et al.; "Weave Patterned Organic Transistors on Fiber for E-Textiles", *IEEE Transactions on Electron Devices*, vol. 52, No. 2, pp. 269-275, (Feb. 2005).

S. Locci et al.; "Woven Electronics: a new perspective for wearable technology", *Proceedings of the 29th Annual Intl. Conf. of the IEEE EMBS*, pp. 3970-3973, (Aug. 23-26, 2007).

A. Schwarz et al.; "Steps Towards a Textile-Based Transistor: Development of the Gate and Insulating Layer", *Textile Research J.*, vol. 80(16), pp. 1738-1746, (Apr. 13, 2010).

* cited by examiner

FIBER-BASED ORGANIC ELECTROCHEMICAL TRANSISTOR

FIELD OF THE INVENTION

The present invention relates to an electrochemical device, and particularly but not exclusively, to an electrochemical transistor device based on conducting organic materials.

BACKGROUND OF THE INVENTION

The transistor is an important building block of electronic devices and has been widely used in the development of various sensors, including electrical and chemical sensors. Among the different types of transistor based sensors, electrochemical transistors (ECTs) have gained particular attentions for their simple and low-cost fabrication, mechanical flexibility and also the adaptability to miniaturization, in contrast to the traditional transistors such as field effect transistors (FETs). Organic materials such as conducting polymers have been used to develop organic electrochemical transistors (OECTs), which facilitate the use of OECTs in the biological and chemical sensing areas.

In contrast to field effect transistors (FETs), in which the detecting mechanism is field driven, i.e., the density of charge carriers between the source and the drain terminals are modulated via capacitive coupling between the gate electrode and the transistor channel, the detecting mechanism of the organic electrochemical transistors (OECTs) is potential driven, i.e., based on electrochemical redox reactions between an electrolyte and the organic electrodes. The switching between an oxidized state and a reduced state during the electrochemical reaction corresponds to a change of conductivity of the transistor, and thereby facilitating the quantification of the analyte in the electrolyte. The operation of the OECTs in electrolytes enables the OECTs to be operable under relatively lower voltages, and thus allows the OECTs to be tailored to specialized applications such as for detection of biological molecules in the physiological environment.

The OECTs offer improved biological and mechanical compatibility when compared to the traditional electronic materials. Particularly, for biosensing applications, it is required that the devices are reliable, robust, miniaturized and inexpensive.

US2013128332 A1 describes an OECT made with multiple planar layers including a substrate, electrodes and a solidified electrolyte layer. US 20120247976 A1 also teaches an OECT made with planar substrates for glucose sensing. These planar OECTs possess practical disadvantages due to their relatively poor flexibility and bulkiness, which prevent them from being used in applications in which flexibility and small-scale operation are essential.

For providing better flexibility to the OECTs, G. Tarabella et la. (G. Tarabella, M. Villani, D. Calestani, R. Mosca, S. Iannotta, A. Zappettini and N. Coppede, *J. Mater. Chem.*, 2012, 22, 23830) developed a cotton thread based OECT for the detection of saline in aqueous solution fabricated by a relatively simple process. X. Tao et la. (X. Tao, V. Koncar and C. Dufour, *J. Electrochem. Soc.*, 2001, 158(5), H572-H577) has also reported the construction of a plastic multifilament based OECT for used in the textile industry.

It is therefore an object of the present invention to provide an organic electrochemical transistor device in which the aforesaid shortcomings are mitigated, or at least to provide a useful alternative.

SUMMARY OF THE INVENTION

In accordance with a first aspect of the present invention, there is provided an electrochemical transistor device comprising a first monofilament; a first conducting layer and an electro-active layer that are substantially coaxial with, and extend circumferentially about, the first monofilament; the first conducting layer comprises a source contact and a drain contact; a gap between the source and the drain contacts of the first conducting layer; wherein the electro-active layer is in electrical contact with the source and the drain contacts, the electro-active layer having a transistor channel interface for contacting with an electrolyte, the electro-active layer being of an organic material capable of altering its electrical conductivity through a change in its redox state; and a gate electrode spaced apart from the first monofilament, wherein current between the source contact and the drain contact is controllable by means of a voltage applied to the gate electrode.

Preferably, the first conducting layer abuts the first monofilament, and the electro-active layer fills the gap.

Preferably, the electro-active layer at least partially covers the source and the drain contacts.

Preferably, the electrochemical transistor device further comprising a dielectric layer that is substantially coaxial with, and extends circumferentially about the monofilament, the dielectric layer comprises a first section and a second section axially spaced apart to expose the transistor channel interface therebetween.

Preferably, the dielectric layer overlies the electro-active layer.

Preferably, the source and the drain contacts, and the first and the second sections of the dielectric layer are substantially cylindrical.

Preferably, the electrochemical transistor device further comprising a second monofilament, wherein the gate electrode comprises a second conducting layer that is substantially coaxial with, and extends circumferentially about, the second monofilament.

Preferably, the transistor channel interface is arranged such that flow of electrons between the source contact and the drain contact is controllable by means of a voltage applied between the gate electrode and one of the source contact and the drain contact.

Preferably, the organic material of the transistor channel interface is such that flow of electrons between the source contact and the drain contact is restrained or promoted upon application of a voltage to the gate electrode.

Preferably, the organic material is a polymer selected from the group consisting of polythiophenes, polypyrroles, polyanilines, polyisothianaphtalenes, polyphenylene vinylenes and copolymers thereof.

Preferably, the organic material comprises poly(3,4-ethylenedioxythiopene) poly(styrene sulfonate).

Preferably, at least one of the first and the second conducting layers comprises a layer of metal or metal compound selected from a group consisting of titanium, platinum, gold, a compound thereof and a combination thereof.

Preferably, at least one of the first and the second conducting layers comprises a first metal layer and a second metal layer, each of the first and the second metal layers comprises metal or metal compound selected from a group consisting of titanium, platinum, gold, a compound thereof and a combination thereof.

Preferably, the dielectric layer comprises poly(p-xylylene).

Preferably, at least one of the first and the second monofilament is a nylon fiber.

Preferably, there is provided a biosensor comprising an electrochemical transistor comprising a first monofilament; a first conducting layer and an electro-active layer that are substantially coaxial with, and extend circumferentially about, the first monofilament; the first conducting layer comprises a source contact and a drain contact; a gap between the source and the drain contacts of the first conducting layer; wherein the electro-active layer is in electrical contact with the source and the drain contacts, the electro-active layer having a transistor channel interface for contacting with an electrolyte, the electro-active layer being of an organic material capable of altering its electrical conductivity through a change in its redox state; and a gate electrode spaced apart from the first monofilament, wherein current between the source contact and the drain contact is controllable by means of a voltage applied to the gate electrode, wherein the gate electrode comprises a gate electrode, a surface of the gate electrode is functionalized with a material comprises biomolecules, nanoparticles, biocompatible polymers, or a combination thereof.

Preferably, the material comprises chitosan, graphene, enzymes, DNA molecules, or a combination thereof.

Preferably, there is provided a method of manufacturing an electrochemical transistor comprising a first monofilament; a first conducting layer and an electro-active layer that are substantially coaxial with, and extend circumferentially about, the first monofilament; the first conducting layer comprises a source contact and a drain contact; a gap between the source and the drain contacts of the first conducting layer; wherein the electro-active layer is in electrical contact with the source and the drain contacts, the electro-active layer having a transistor channel interface for contacting with an electrolyte, the electro-active layer being of an organic material capable of altering its electrical conductivity through a change in its redox state; and a gate electrode spaced apart from the first monofilament, wherein current between the source contact and the drain contact is controllable by means of a voltage applied to the gate electrode, the method comprising steps of fabricating a first electrode and a second electrode, wherein the step of fabricating the first electrode comprising: depositing a conductive material on at least two axial ends of a first monofilament to form a source contact and a drain contact; depositing an electro-active material to cover the first monofilament and at least partially the source contact and the drain contact to form an electro-active layer; depositing a dielectric material on two axially spaced apart sections of the electro-active layer and forming a transistor channel interface therebetween.

Preferably, the step of fabricating the second electrode comprising: depositing a conductive material on at least two axial ends of a second monofilament to form an conducting end and a gate electrode; depositing a dielectric material to cover the second monofilament and at least partially the conducting end and the gate electrode.

Preferably, the method further comprising step of immobilizing a bio-active material onto a surface of the gate electrode.

Preferably, the method further comprising a step of masking at least a section of the first or the second monofilament prior to the step of depositing the conductive material.

Preferably, the step of depositing the conductive material is performed by sputter deposition.

Preferably, the method comprising a step of treating with oxygen plasma after the step of depositing the conductive material.

Preferably, the step of depositing an electro-active material is performed by drop coating.

Preferably, the method further comprising a step of drying the electro-active material.

Preferably, the method further comprising a step of masking at least a section of the electro-active layer prior to the step of depositing the dielectric material.

Preferably, the method further comprises a step of masking the gate electrode prior to the step of depositing the dielectric material.

Further aspects of the invention will become apparent from the following description of the drawings, which are given by way of example only to illustrate the invention.

BRIEF DESCRIPTION ON THE DRAWINGS

Figure 1:
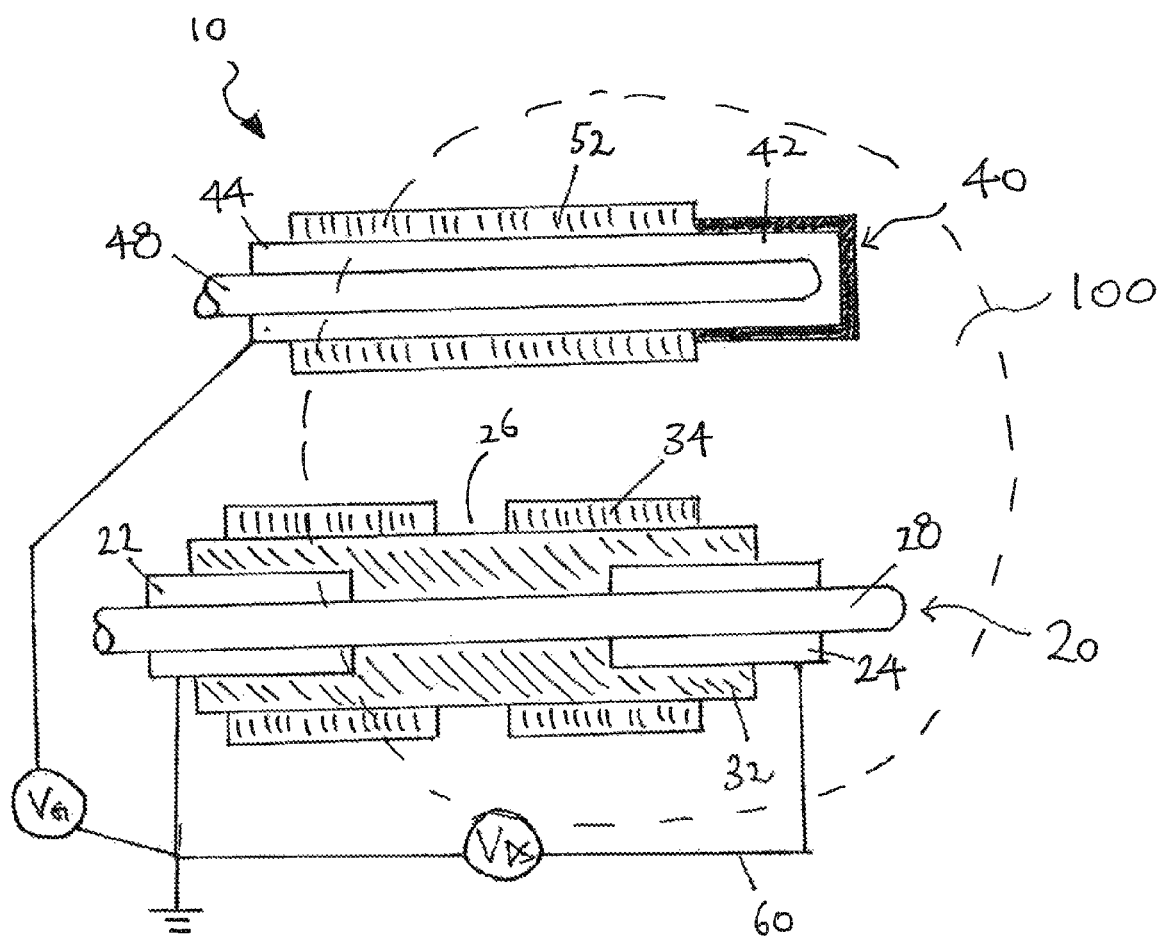
FIG. 1 is a schematic sectional view showing the organic electrochemical transistor (OECT) as embodied in the present invention.
Figure 2:
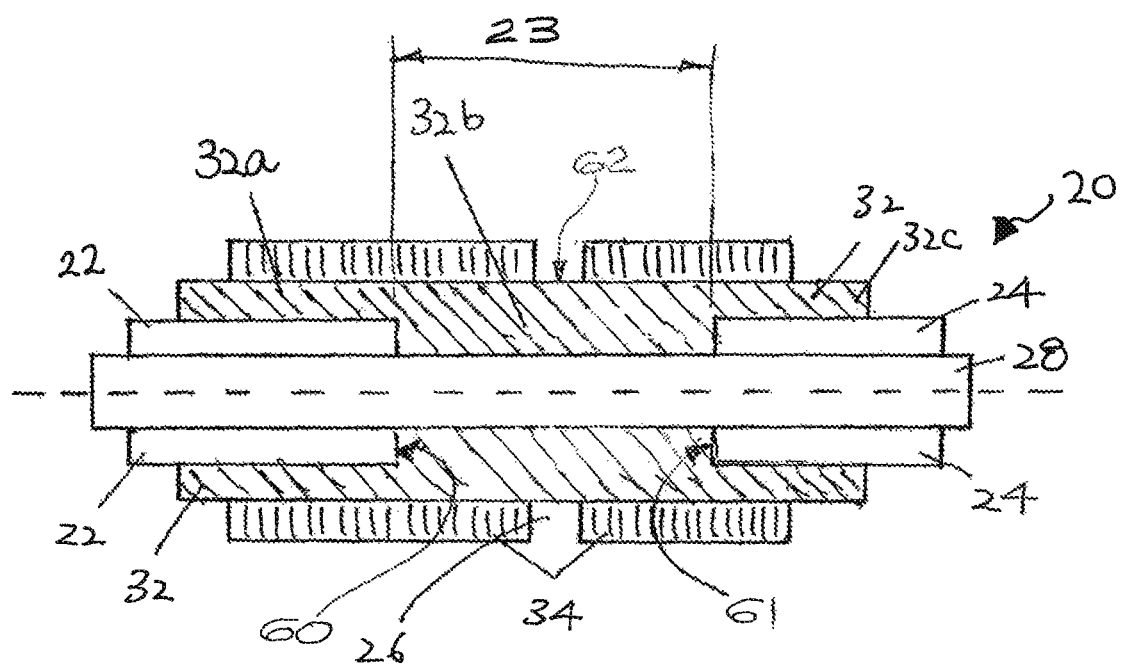
FIG. 2 is a schematic longitudinal section showing the layers of a first part of the OECT of FIG. 1 that includes the source and drain contacts.
Figure 7:
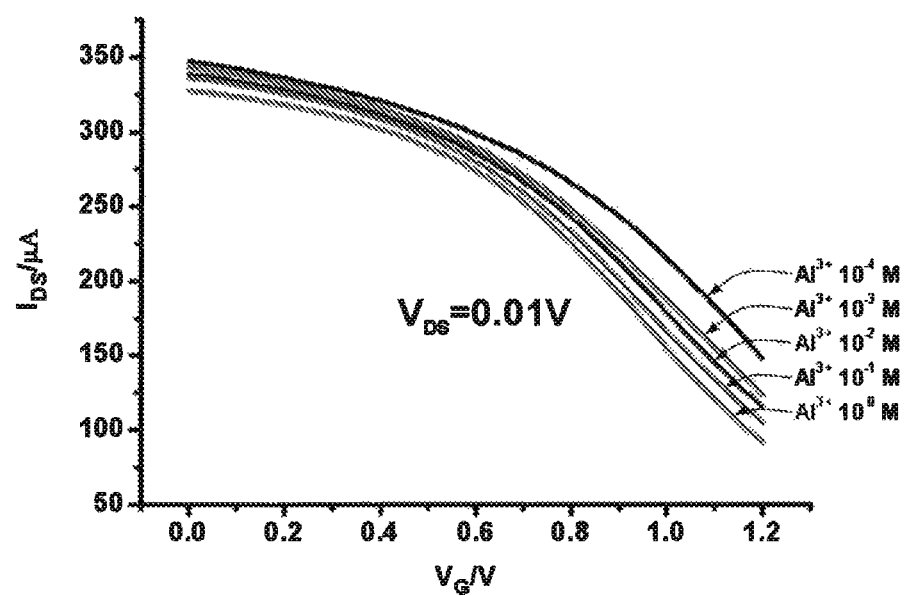
Figure 8:
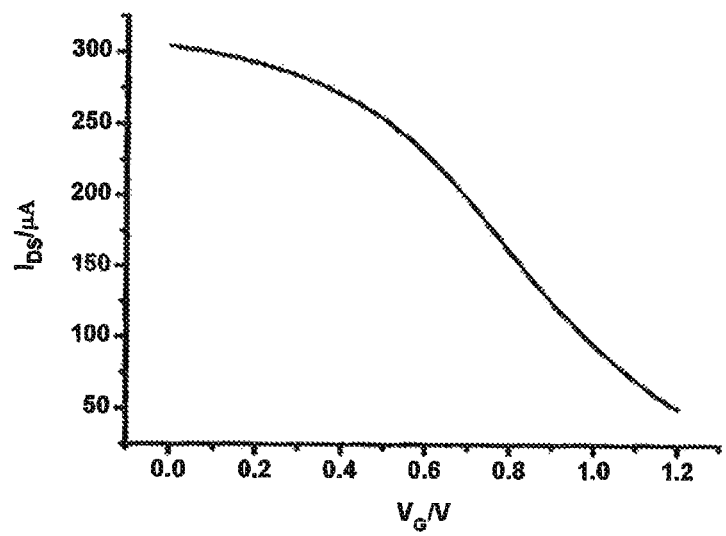
Figure 8B:
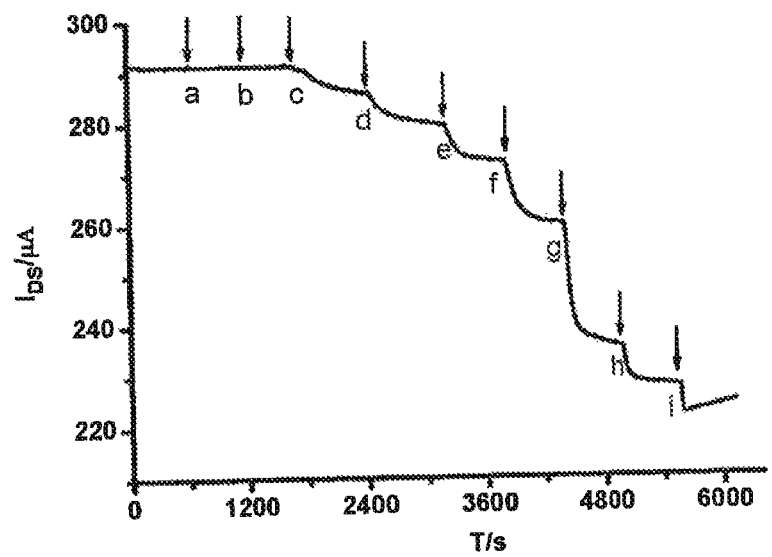
Figure 8:
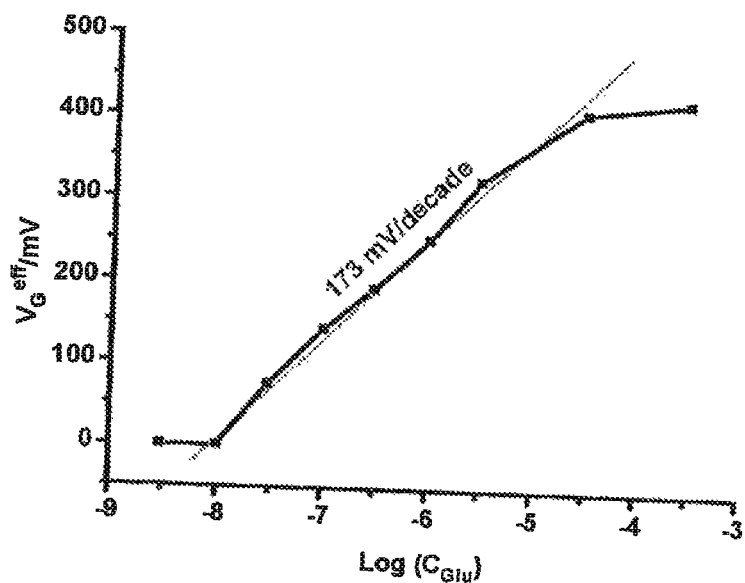
Figure 8D:
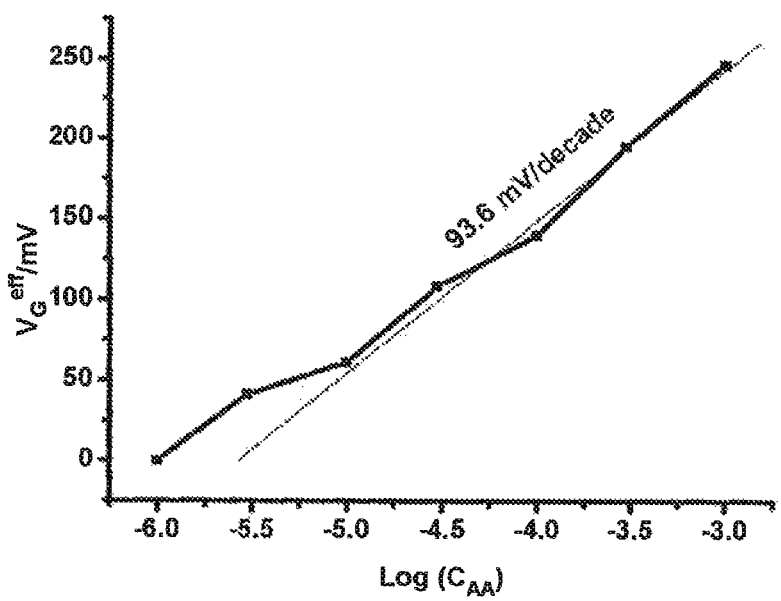
Figure 8:
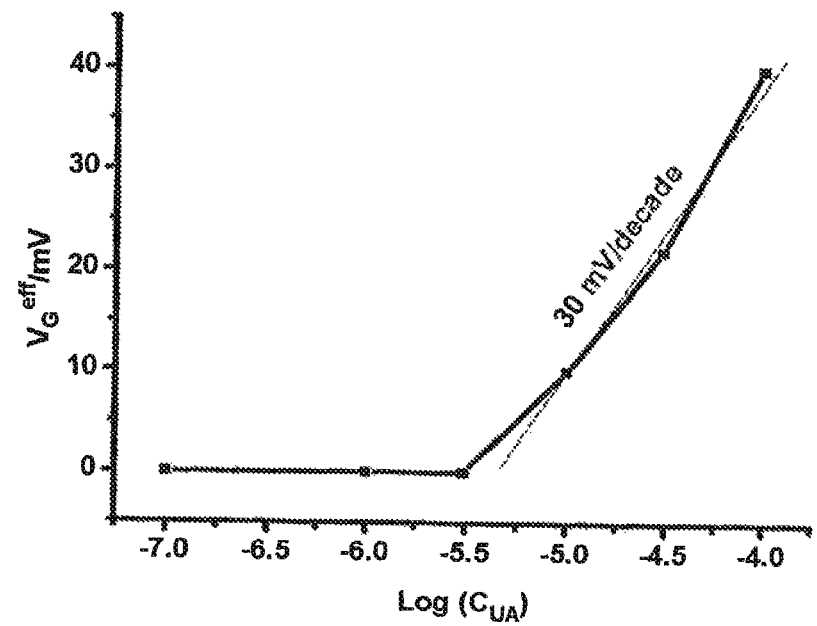
Figure 8:
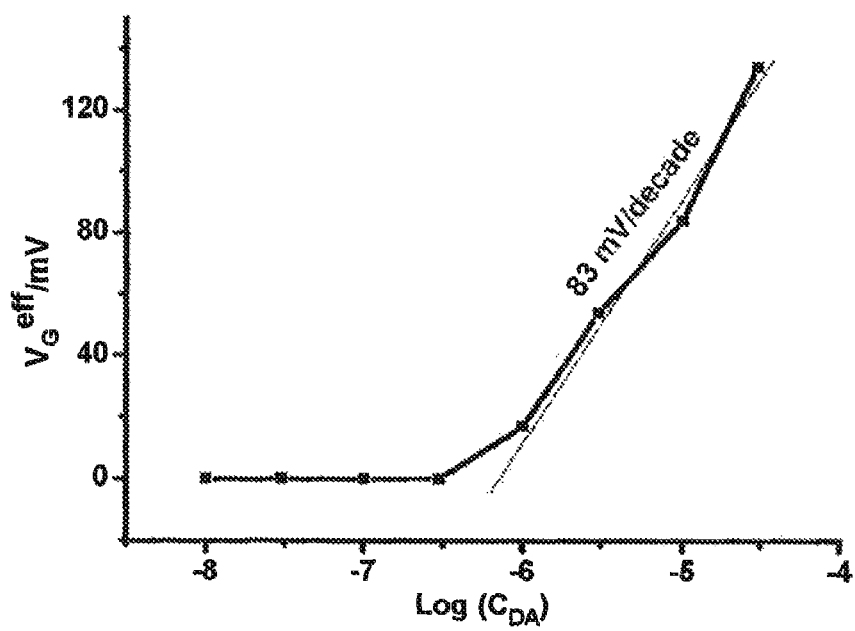

FIG. 7 shows a transfer curve ($I_{DS}$-$V_G$) of the OECT of FIG. 1 measured in $Al^{3+}$ solutions with different ion concentrations; and FIGS. 8(a) to 8(f) show the responses of the OECT of FIG. 1 to the additions of glucose, uric acid, ascorbic acid and dopamine in PBS solutions. FIG. 8(a) is a transfer curve ($I_{DS}$-$V_G$) of the OCET with modified gate electrode measured in PBS solution. FIG. 8(b) shows channel current response of the OECT with modified gate electrode to the additions of glucose in PBS solution. From the additions of a to i, the concentrations of glucose in the PBS solution are 3 nM, 10 nM, 30, 100 nM, 300 nM, 1000 nM, 3 μM, 30 μM and 300 μM, respectively. FIG. 8(c) shows changes of the effective gate voltage of the OECT as a function of glucose concentrations. FIG. 8(d) shows changes of the effective gate voltage of the OECT as a function of ascorbic acid (AA) concentrations. FIG. 8(e) shows changes of the effective gate voltage of the OECT as a function of uric acid (UA) concentrations. FIG. 8(f) shows changes of the effective gate voltage of the OECT as a function of dopamine (DA) concentrations.

DETAILED DESCRIPTION ON THE PREFERRED EMBODIMENT

The following description is given by way of example only to illustrate embodiments of the invention. The terminology used is for illustrative purpose only, and is not intended to limit the scope or use of the invention, unless the text clearly and explicitly requires otherwise.

Referring to FIG. 1, the organic electrochemical transistor (OECT) 10 of the present invention includes two elongate parts formed on respective lengths of fiber 28, 48: a drain/source assembly 20, comprising axially spaced apart source and drain contacts 22, 24, and a gate electrode assembly 40 comprising a gate electrode 42. In use, the drain/source assembly 20 and gate electrode assembly 40 are placed in an electrolyte 100 and electrically connected via an external circuit 60.

A monofilament fiber 28, 48, such as a nylon fiber, forms the substrate upon which both the drain/source assembly 20 and the gate electrode assembly 40 are built up in circumferential layers, using a layer-by-layer fabrication technique. The fibers 28, 48 can be of a diameter of, for example, 0.3 mm to 0.5 mm, but it should be understood that the invention is not limited to the use of fibers of these dimensions or material. A first layer of electrically conductive material is applied directly to the fibers 28, 48 to form the source contact 22, the drain contact 24, and the gate electrode 42.

The source contact 22 and the drain contact 24 of the source/drain assembly, and the gate electrode 42 are substantially coaxial with, and extend circumferentially about, the corresponding monofilament fibers 28, 48. The monofilament fibers 28, 48 may have a generally circular cross-section of constant diameter throughout their length, with the source and drain contacts 22, 24 and the gate electrode 42 having a complementary inner surface abutting the fibers and a generally constant thickness in the radial direction, so as to have a substantially cylindrical form. Adjacent axial ends 60, 61 of the source and drain contacts 22, 24 may have an annular form aligned in respective radial planes (not shown).

During fabrication, a central region of the plastic fiber 28 is first masked circumferentially. A conducting layer of metal may then be applied the plastic fiber 28 by sputtering, such that removal of the mask leaves a gap 23 in the metal layer, to form the separate source and drain contacts 22, 24. The gap 23 extends axially between the contact ends 60, 61. The metal layer forming the source and drain contacts 22, 24 and electrode 42 can be prepared by sequential sputtering of a first titanium layer followed with a second gold or platinum layer. The titanium layer can be of a thickness of about 10 nm, and the gold or platinum layer can be of a thickness of 100 nm. The purpose for coating the first titanium layer prior to the second gold or platinum layer is to enhance adhesion of the second layer. The metal-coated plastic fiber is then treated with oxygen plasma for about 5 mins for cleaning the surface of the coated fiber.

After the oxygen plasma treatment, the metal-coated fiber is coated with a layer of poly(3,4-ethylene di-oxythiophene): poly(styrene-sulfonate) (PEDOT:PSS) 32 to provide the electro-active layer. Alternatively, organic semiconducting material such as polythiophenes, polypyrroles, polyanilines, polyisothianaphtalenes, polyphenylene vinylenes and copolymers thereof can also be used.

Specifically, a solution of PEDOT:PSS is dropped on the surface of the metal-coated fiber, which covers part of the source contact 22, part of the drain contact 24 and the area of the plastic fiber 28 therebetween which was not coated with metal in the previous step, to form the gap 23. The PEDOT: PSS layer 32 thus fills the gap 23 and covers part of the source and drain contacts 22, 24. The PEDOT:PSS layer 32 forms a continuous layer circumferentially and thus is generally cylindrical, and it includes: (1) thinner regions 32a, 32c at its axially opposing ends that surround parts of the source contact 22 and drain contact 24; and (2) a thicker region 32b which fills the gap 23, abuts the two ends 60, 61, and surrounds the uncoated surface of the fiber 28. The PEDOT:PSS coated fiber may then be dried in a glove box filled with high purity nitrogen gas for an annealing process for 1 hour at an elevated temperature of about 100-120° C.

After annealing, the PEDOT:PSS coated fiber is cooled to room temperature. A layer of dielectric material such as parylene 34, i.e., polyp-xylylene) is then coated on the PEDOT:PSS coated fiber, with a central region of the PEDOT:PSS layer axially located between the two axial ends 60, 61 being masked to form an annular active channel 26. The active channel 26 is of a width less than the width of the gap 23, and allows exposure of an annular interface 62 of the PEDOT:PSS which is capable of alternating its electrical conductivity through a change in its redox state when the electrodes 20 and 40 are electrically connected. The parylene layer 34, like the other layers, is substantially coaxial with and extends circumferentially about the plastic fiber 28, and serves as a cylindrical barrier for protecting and packaging the electrode assembly 20.

Figure 3A:
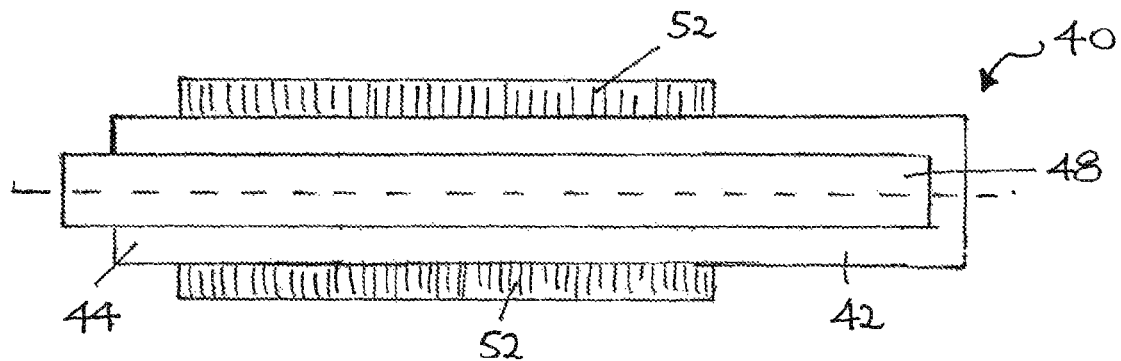
FIG. 3A is a longitudinal section showing the layers of a second part or gate electrode of the OECT of FIG. 1, without the surface of the gate electrode being functionalized.

When fabricating the gate electrode assembly 40 as shown in FIG. 3A, the fiber 48 is first coated with a continuous layer of metal using the same technique used to make the source/drain electrode assembly 20 as discussed above. One end of the fiber 48 may be completely metal coated to serve as the gate electrode 42, and the opposite end 44 is used to connect with the circuit 60 so that current between the source 22 and the drain 24 contacts will be controllable when a voltage is applied to the gate electrode 42. The flow of electrons between the source 22 and the drain 24 contacts will be restrained or promoted upon application of a voltage to the gate electrode 42.

After the metal coating, one end of the gate electrode 42 may be masked, and a layer of dielectric material such as parylene 52 is then coated directly onto the metal coated fiber 48 to circumferentially overlie part of the gate electrode 42 for packaging and protecting purposes.

Figure 3B:
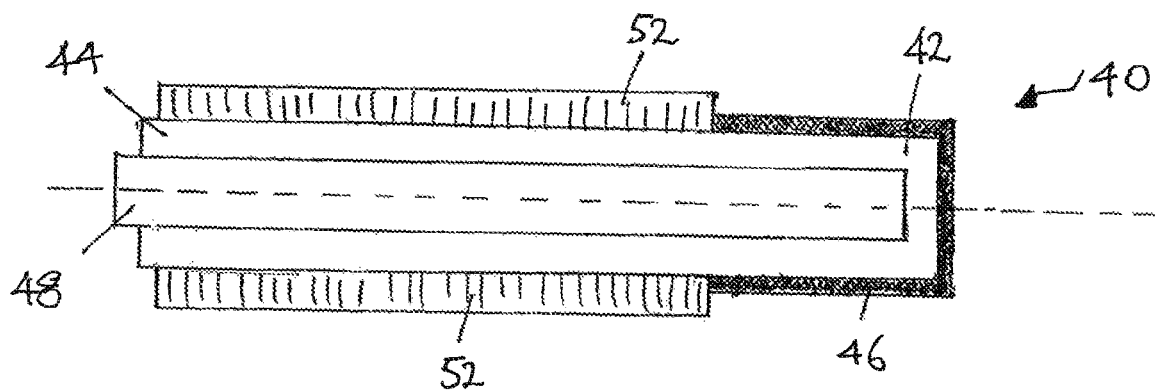
FIG. 3B is a schematic longitudinal section showing the layers of the gate electrode of the OECT of FIG. 1 with the surface of the gate electrode being functionalized.

To serve as a biosensor for sensing biomolecules, the gate electrode 42 may be functionalized by immobilizing bioactive materials on its exposed outer surface 46, as shown schematically in FIG. 3B. For example, a gate electrode having a Ti/Pt coated surface may be further modified with nanomaterials, biocompatible polymers and enzymes to detect ions or glucose, and a gate electrode having a Ti/Au coated surface further modified with DNS probes can be used to detect the target DNA molecules. During measurements, the gate electrode 42 and the active channel 26 are brought into contact with an aqueous electrolyte carrying the analytes (e.g. glucose, dopamine, uric acid, DNA, etc.).

In testing, the source terminal of the OECT 10 was grounded while the gate electrode 42 and drain 24 was connected to two Keithley source meters (Keithley 2400) to apply voltages to the gate and drain. The response of the OECT 10 was determined under various gate voltages ($V_G$) and source-drain voltages ($V_{DS}$) controlled by a Labview computer program. For transfer characteristics, the drain current ($I_{DS}$) between source 22 and drain 24 contacts was measured as a function of $V_G$ at a fixed $V_{DS}$. The response to the addition of analytes was measured at constant $V_G$ and $V_{DS}$ as a function of time.

EXAMPLE

Materials

Glucose oxidase (GOx) (50 kU g$^{-1}$) was obtained from Aladdin Reagent Database Inc. and stored at −20° C. for future use. Phosphate buffered saline (PBS) solution (pH 7.4), PEDOT:PSS and Nafion aqueous solution were all obtained from Sigma-Aldrich Co. and stored at 4° C. condition. Chitosan (CHIT) was purchased from Advanced Technology & Industrial Co., Ltd and used as received. Glucose oxidase (GOx) stock solution (10 mg mL$^{-1}$) in PBS was stored in a refrigerator (4° C.). Glucose, L-ascorbic acid (AA) and uric acid (UA) were also purchased from Sigma Aldrich Co. Solution-based graphene fakes with an average size of several micrometers were prepared by ultrasonic exfoliation from graphite. Reduced graphene oxide (rGO) was chemically synthesized by exfoliation and in-situ reduction of graphite with sodium dodecylbenzene sulfonate as the stabilizing agent. Graphene and rGO were dispersed in deionized water for later use and were stored in ambient environment.

Fabrication of the Multi-Layers Structure of the Electrodes

Firstly, titanium and gold or platinum metals were deposited on the two distal ends of two plastic nylon fibers (Φ300 μm) by RF magnetron sputtering. The thin layer of Ti (thickness: about 10 nm, sputtered for 5 mins) serves as the adhesion layer for the Au or Pt thin film (thickness: about 100 nm, sputtered for 5 mins). Before the sputtering, a tape was used to mask a region between the two ends of each of the fiber so that a region which was not coated with metal was formed between the two ends on the fiber. The Ti/Au coated plastic fibers were treated with oxygen plasma (at 20 W) for about 5 mins. These metal-coated fibers will then serve as the core of the source/drain electrode assembly having the source contact, the drain contact and the active channel, and the gate electrode having the gate electrode.

For the preparation of the source/drain electrode assembly, a thin layer of PEDOT:PSS was drop coated onto the Ti/Au or Ti/Pt coated fiber, covering the areas of two metal-coated ends (i.e., the source and drain contacts) and the fiber surface which was not coated with metal in the previous step. The PEDOT:PSS coated fiber was then moved to a glove box filled with high purity nitrogen for an annealing process (120° C., 1 hour). After the annealing process, the PEDOT:PSS coat was cooled to room temperature, and a thin layer of parylene (thickness: about 1 μm) was deposited on the PEDOT:PSS coated fiber using the parylene deposition system (SCS PDS 2010E Labcoter). Prior to the parylene deposition procedure, a tiny tape was used to mask an area of approximately 200 μm in width on the PEDOT:PSS surface to provide an active PEDOT:PSS channel between the two contacts.

For the preparation of the gate electrode having the gate electrode, one of the Ti/Au or Ti/Pt coated end of the metal coated plastic fiber was first masked with a tape, which will later be served as the gate electrode. After that, a thin parylene film (thickness: about 1 μm) was coated directly onto the surface of the fiber. The masking allows the gate electrode to be parylene-free, which will be available for further surface modification with probing materials in the next step.

Modification of Gate Electrodes

Preparation of the Glucose Sensors

To prepare a glucose sensor based on the fabricated fiber-based OECT, surface of the gate electrode was further modified with a biocompatible polymer chitosan (CHIT), graphene flakes and enzymes. For example, in the preparation of a CHIT/glycose oxidase (GOx)/Pt gate electrode, 10 mL of a solution of GOx in phosphate buffered saline (PBS) was drop-coated on the surface of the Pt gate electrode, and the gate electrode was left dry at 4° C. Then 50 mL of a solution of CHIT in acetic acid (CHIT 5 mg mL$^{-1}$; acetic acid: 50 mM, pH: 5-6) and 50 ml of a graphene aqueous solution were uniformly mixed to form a CHIT-graphene solution mixture. The GOx/Pt gate electrode was then drop-coated with 10 mL of the CHIT-graphene solution mixture and left dry in a refrigerator. When the modified CHIT/glycose oxidase (GOx)/Pt gate electrode was formed, the gate electrode was immersed in a PBS solution and stored at 4° C. for later use.

Preparation of Other Sensors

To prepare OECT sensors for dopamine, uric acid (UA) and DNA, the gate electrode was modified using similar surface modification techniques as discussed above.

Device Characterization

For ions detection, the electrodes were connected to two Keithley source meters (Keithley 2400) and measured under various gate voltages ($V_G$, 0-1.2V) and a fixed source-drain voltages ($V_{DS}$, 0.01V). The electrodes were then dipped in beakers filled with aqueous solutions with different ion concentrations for device characterization.

For glucose detection, prior to the device characterization, the modified gate electrode was thoroughly rinsed with a PBS solution to remove any undesired residues left on the electrode. After that, the active channel of the source/drain electrode and the modified gate electrode of the gate electrode were immersed in a PBS solution filled in a 10 mL beaker before the measurement. A designed amount of glucose solutions of increasing concentrations ($10^{-5}$ M to $10^0$ M) was slowly added into the PBS solution to obtain various concentrations of glucose in the PBS. The source, drain and gate electrode s of the electrodes were connected to two Keithley source meters (Keithley 2400) and the solution was measured under various gate voltages ($V_G$) and source drain voltages ($V_{DS}$) controlled by a Labview computer program. For transfer characteristics, the channel current ($I_{DS}$) between the source and drain contacts was measured as a function of $V_G$ (0 to 1.2 V) at a fixed $V_{DS}$ (0.01 V). The real-time responses of the OECT sensor to each of the addition of the glucose solutions were measured at constant $V_G$ (0.4 V) and $V_{DS}$ (0.01 V) as a function of time.

For other applications such as dopamine, uric acid (UA) and DNA sensing, the set up of the sensor and the measurement conditions are similar to the above glucose detection experiment.

Results and Discussion

I-V Transfer Characteristic in PBS Solution

Figure 4:
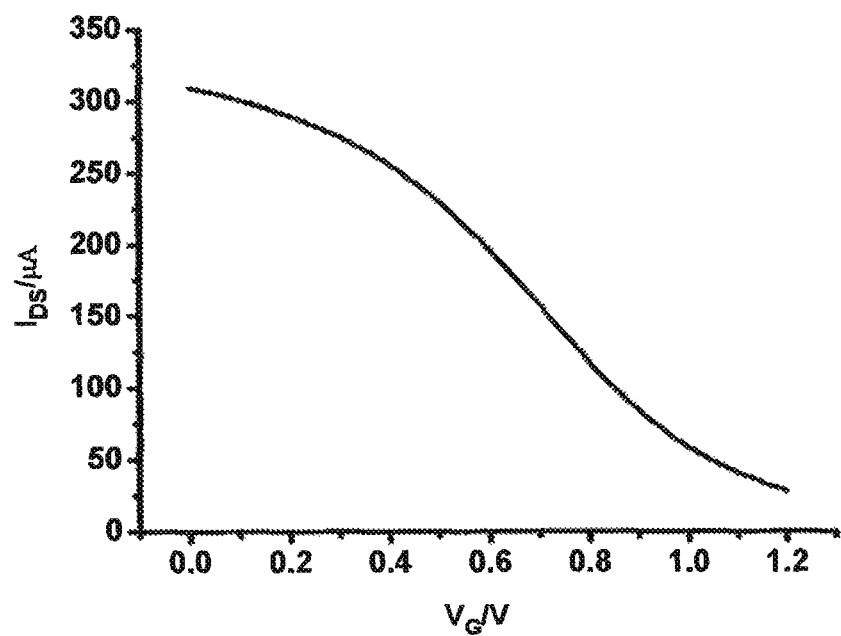
FIG. 4 shows a transfer curve ($I_{DS}$-$V_G$) of the OECT of FIG. 1 characterized in a standard PBS solution.

FIG. 4 shows a transfer curve ($I_{DS}$-$V_G$) of the embodied OECT characterized in a standard PBS solution. Poly(3,4-ethylenedioxythiophene):poly(styrenesulfonate) (PEDOT:PSS), which is one of the most-widely used p-type organic semiconductors in OECT-based sensors, has demonstrated a wide range of electric conductivities due to the varied doping level of counter ions (Peng Lin and Feng Yan, *Adv. Mater.* 24, 34-51 (2012)). When a positive gate voltage is addressed, cations in the electrolyte will be injected into the active PEDOT:PSS film in the channel, and then modulate the carrier density in the PEDOT:PSS film. The migration of the cations from the electrolyte to the PEDOT:PSS film can be regarded as a de-doping process that reduces the density of hole and thus reduce the electric conductivity of the deposited polymer layer. Details on the de-doping process can be found using the following electrochemical reaction (Caizhi Liao, Feng Yan, *Polymer Reviews,* 53, 352-406 (2013)):

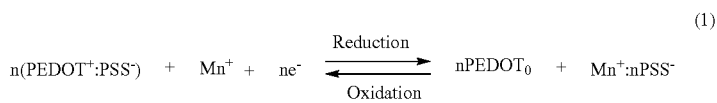

(1)

where Mn$^+$ represents the cation in the electrolyte, n is the number of charge of the cation, e is the electron. The injection of $Mn^+$ to the active layer induces the reduction of the oxidized $PEDOT^+$ (highly conductive) to the neutral state $PEDOT^0$ (low conductivity), leading to the much decreased channel current.

As shown in FIG. 4, when the gate voltage ($V_G$) was increased from 0 to 1.2 V, more ions will be injected into the PEDOT:PSS film, inducing a reduced conductivity of the active layer and thus a reduced in the channel current ($I_{DS}$). It is observed that the channel is highly conductive at the zero gate voltage ($V_{DS}$=0.01 V) and that the channel current approaches zero when $V_G$ is at 1.2 V. The gate electrode being used in this experiment was unmodified, i.e., was a bare Ti/Pt coated gate electrode.

Ions Detection

Figure 5:
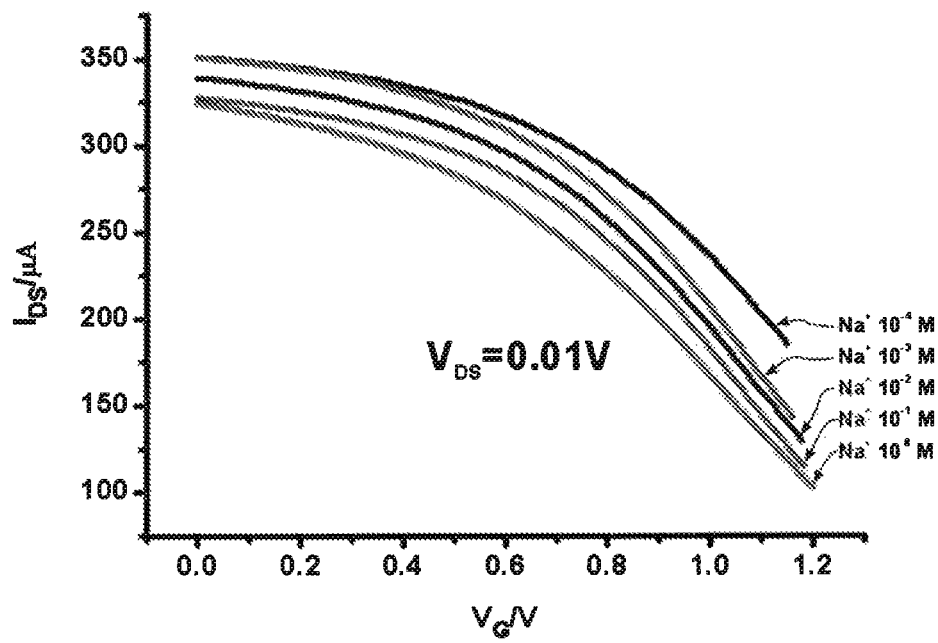
FIG. 5 shows a transfer curve ($I_{DS}$-$V_G$) of the OECT of FIG. 1 measured in $Na^+$ solutions with different ionic concentrations.
Figure 6:
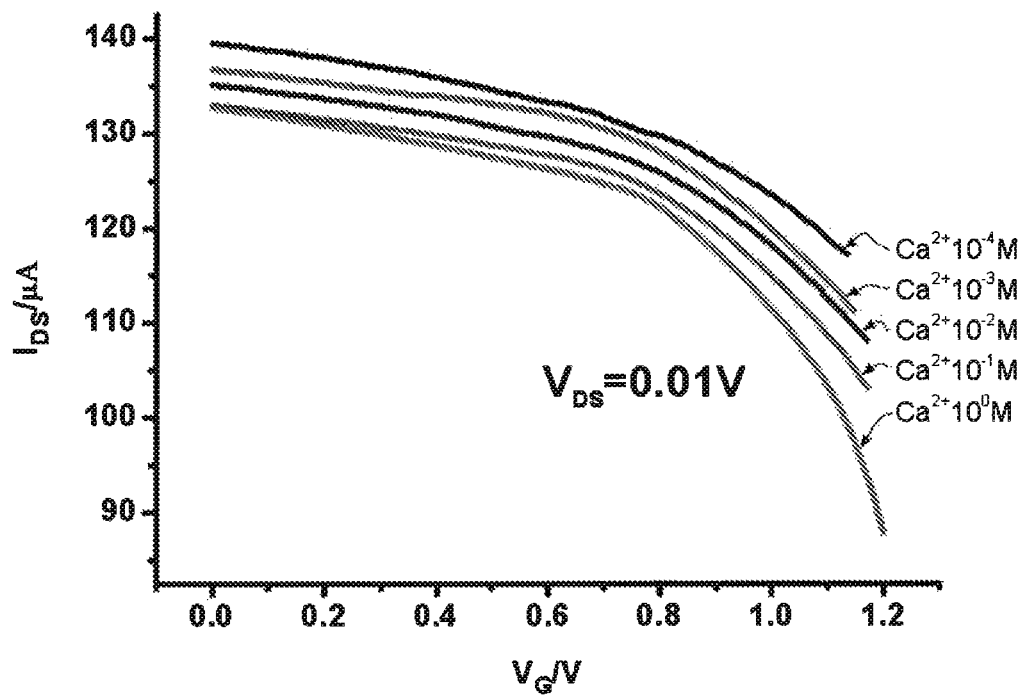
FIG. 6 shows a transfer curve ($I_{DS}$-$V_G$) of the OECT of FIG. 1 measured in $Ca^{2+}$ solutions with different ion concentrations.

The ions detection by the OECT sensor as embodied in the present invention can be shown in FIGS. 5 to 7. FIG. 5 illustrates a graph showing the transfer curves ($I_{DS}$-$V_G$) of the embodied OECT sensor measuring $Na^+$ solutions with different ion concentrations. The $Na^+$ concentrations are $10^{-4}$M (Black curve), $10^{-3}$M (Red curve), $10^{-2}$M (Blue curve), $10^{-1}$M (Green curve), $10^0$ M (Pink curve). FIG. 6 illustrates a graph showing the transfer curves ($I_{DS}$-$V_G$) of the embodied OECT sensor measuring $Ca^{2+}$ solutions with different ion concentrations. The $Ca^{2+}$ concentrations are $10^{-4}$M (Black curve), $10^{-3}$M (Red curve), $10^{-2}$M (Blue curve), $10^{-1}$M (Green curve), $10^0$M (Pink curve). FIG. 7 further illustrates a graph showing the transfer curves ($I_{DS}$-$V_G$) of the embodied OECT sensor measuring $Al^{3+}$ solutions with different ion concentrations. The $Al^{3+}$ concentrations are $10^{-4}$M (Black curve), $10^{-3}$M (Red curve), $10^{-2}$M (Blue curve), $10^{-1}$M (Green curve), $10^0$M (Pink curve).

FIGS. 5 to 7 demonstrate the responses of the OECT sensor to different level of metal ions. The gate electrode s being used in these experiments were unmodified, i.e., were bare Ti/Pt coated gate electrode s. Similar to the I-V transfer curves of the unmodified OECT sensor measuring the PBS solution as shown in FIG. 4, the I-V response curves are shown to shift to a lower value with an increased level of ions. When the electrodes were immersed in a solution of a higher ion concentration, more ions will be injected into the active semi-conductor PEDOT:PSS film in the channel at fixed voltages, and thus induce a reduced channel current according to Equation (1).

Glucose Detection

Nanomaterials can be used to improve the electrochemical activity of the gate electrode and thus enhance the sensitivity of the OECT sensor. In a further embodiment, the gate electrode has been further modified with graphene flakes synthesized by an economical chemical method [K. H. Park, et al. *Nano Lett.* 2012, 12, 2871-2876]. FIGS. 8(*a*)-8(*f*) illustrate the responses of the embodied OECT sensor having a CHIT-Graphene-GOx modified Ti/Pt gate electrode to the additions of glucose, uric acid (UA), ascorbic acid (AA) and dopamine (DA) in PBS solutions. Specifically, FIG. 8(*a*) shows a transfer curve ($I_{DS}$-$V_G$) of the OECT sensor in the PBS solution. FIG. 8(*b*) shows a channel current response of the sensor to the additions of glucose in the PBS solution. The arrows a to i show the additions of glucose solution at the concentrations of 3 nM, 10 nM, 30 nM, 100 nM, 300 nM, 1000 nM, 3 μM, 30 μM and 300 μM, respectively. FIG. 8(*c*) shows the change of the effective gate voltage of the sensor as a function of glucose concentrations. The detection limit of glucose is found to be 30 nM, which is approximately two orders of magnitude better than that of the conventional electrochemical sensors using similarly modified electrodes. The change of the effective gate voltage of the sensor as a function of glucose concentrations is 173 mV per decade, demonstrating the highest response among these analytes. More importantly, the gate electrode-modified sensor shows a good linearity in the wide glucose ranges of 30 nM to 30 μM, which covers the normal range of glucose level in human saliva and body fluids. The enhancement of the sensitivity of the modified gate electrode can be attributed to the unique properties of the graphene flakes at the composite film at the gate electrode. Firstly, the high conductivity of graphene facilitates the charge transfer during the reaction. Secondly, the large surface area to volume ratio of the composite film may assist in increasing the load of enzyme. The OECTs glucose sensor with the gate electrode modified with CHIT-graphene/GOx also demonstrates high selectivity toward glucose detection, which is a critical parameter for the real application in clinic diagnosis.

Ascorbic Acid, Uric Acid and Dopamine Detection

Errors from the most-common bioactive interferents, including ascorbic acid (AA), uric acid (UA) and dopamine (DA), are nearly negligible in the practical applications due to the detection limits of the conventional biosensors. FIGS. 8(*d*) to 8(*f*) demonstrate the responses of the gate electrode-modified OECT sensor toward the additions of AA, UA and DA, respectively in the PSB. FIG. 8(*d*) shows that the sensor began to respond to the addition of AA at a concentration of 3 μM, which is much higher than that of the detection limit of glucose. FIGS. 8(*e*) and 8(*f*) demonstrate the interference signals upon the UA and DA additions. The detection limit of UA and DA are 10 μM and 1 μM, respectively, which are much higher than the glucose detection limit, indicating that the OECT sensor shows a much higher sensitivity toward glucose detection. More interestingly, the response of the sensor having a modified gate electrode toward the interferents addition is much reduced when compared with the sensor with an unmodified gate electrode. As shown in FIG. 8(*e*), the OECT sensor with modified gate electrode only shifts for 30 mV per decade upon the UA addition, indicating that interference signals from UA is nearly blocked when the real concentration level in human fluids is taken into consideration. The high selectivity of the sensor may largely attribute to the electrostatic force between the analytes and the composite layers on the modified gate electrode. The isoelectric point of the CHIT is about 6.4, while the isoelectric point of the GOx is about 4.2. Accordingly, the anionic GOx molecules can adhere strongly to the positively charged CHIT surface when the pH of solution is in the range of 4.2-6.4, and thus forming a stable CHIT-GOx ion-pairs. As a result, the GOx can be effectively immobilized on the surface of the CHIT. When the CHIT-graphene/GOx/Pt gate electrode was immersed in the PBS solution (pH 7.4, larger than the isoelectric point of the CHIT) during the electric measurements, the negatively charged CHIT effectively repelled the negatively charged interference species, e.g. UA and AA, due to their electrostatic interaction. Therefore, the sensitivity and response of the modified OECT sensor toward UA and AA additions is much reduced. Although dopamine (DA) is theoretically positively charged in the PBS solution and is likely to be concentrated nearly the surface of the modified gate electrode, the sensor still show a small response to the DA addition. The low response toward DA can be explained by the overwhelming CHIT blocking effects on the modified gate electrode.

All of the embodied fiber-based OECT sensors of the present invention can be used for more than 5 times with similar performance, which is suitable for disposable applications. By modifying the gate electrode, the plastic fiber-based OECT can selectively show response to various chemical and biological analytes to allow multi-functional detections, including high performance UA, DA, DNA and nerve cell sensors, etc.

The fiber-based OECT sensors of the present invention are based on monofilament plastic fibers, which are flexible, small-scale, light-weight, and low cost. In addition, the fabrication procedure is simple, economical and environmental friendly when compared with the conventional photolithography technique. Furthermore, the fiber-based OECT sensors are versatile, which can be easily integrated with complex, solution-based systems such as microfluidic system, medical injection system and implanted device.

Last but not least, the fiber-based OECT sensors of the present invention are operable at ultra-low voltage, such as $V_{DS}$=0.01V, $V_G$ less than 1V, and are adapted to conduct detection in a solution-based environment, which are critical for medical applications and sensing in the human body.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided or separately or in any suitable subcombination.

The invention claimed is:

1. An electrochemical transistor device comprising:
   a first monofilament and a second monofilament, wherein at least one of the first and second monofilaments is a nylon fiber;
   a first conducting layer and an electro-active layer that are substantially coaxial with, and extend circumferentially about, the first monofilament, wherein
      the first conducting layer comprises a source contact and a drain contact and includes a gap between the source contact and the drain contact,
      the electro-active layer is in electrical contact with the source contact and the drain contact,
      the electro-active layer has a transistor channel interface for contacting an electrolyte, and
      the electro-active layer is an organic material having an electrical conductivity altered by a change in redox state of the electro-active layer; and
   a gate electrode spaced from the first monofilament and comprising a second conducting layer that is substantially coaxial with, and extends circumferentially about, the second monofilament, wherein current flow between the source contact and the drain contact is controllable by a voltage applied to the gate electrode.

2. The electrochemical transistor device of claim 1, wherein
   the first conducting layer abuts the first monofilament, and
   the electro-active layer fills the gap.

3. The electrochemical transistor device of claim 2, wherein the electro-active layer at least partially covers the source and drain contacts.

4. The electrochemical transistor device of claim 1, further comprising a dielectric layer that is substantially coaxial with, and extends circumferentially about, the first monofilament, wherein the dielectric layer comprises a first section and a second section axially spaced apart and exposing the transistor channel interface between the first and second sections.

5. The electrochemical transistor device of claim 4, wherein the dielectric layer overlies the electro-active layer.

6. The electrochemical transistor device of claim 4, wherein the source and drain contacts, and the first and second sections of the dielectric layer are substantially cylindrical.

7. The electrochemical transistor device of claim 4, wherein the dielectric layer comprises poly(p-xylylene).

8. The electrochemical transistor device of claim 1, wherein the transistor channel interface is arranged such that flow of electrons between the source contact and the drain contact is controllable by a voltage applied between the gate electrode and one of the source contact and the drain contact.

9. The electrochemical transistor device of claim 1, wherein the organic material restrains or promotes flow of electrons between the source contact and the drain contact in response to application of the voltage to the gate electrode.

10. The electrochemical transistor device of claim 1, wherein the organic material is a polymer selected from the group consisting of polythiophenes, polypyrroles, polyanilines, polyisothianaphtalenes, polyphenylene vinylenes, and copolymers thereof.

11. The electrochemical transistor device of claim 10 wherein the organic material comprises poly(3,4-ethylenedioxythiopene) poly(styrene sulfonate).

12. The electrochemical transistor device of claim 1, wherein at least one of the first and second conducting layers comprises a layer of a metal or a metal compound selected from the group consisting of titanium, platinum, gold, an alloy thereof, and combinations thereof.

13. The electrochemical transistor device of 1, wherein
   at least one of the first and second conducting layers comprises a first metal layer and a second metal layer, and
   each of the first and second metal layers comprises a metal or a metal compound selected from the group consisting of titanium, platinum, gold, an alloy thereof, and combinations thereof.

14. A biosensor comprising an electrochemical transistor according to claim 1, wherein a surface of the gate electrode is functionalized with a material selected from the group consisting of biomolecules, nanoparticles, biocompatible polymers, and combinations thereof.

15. The biosensor of claim 14, wherein the material functionalizing the surface of the gate electrode is selected from the group consisting of chitosan, graphene, enzymes, DNA molecules, and combinations thereof.

* * * * *